United States Patent
Eriksson

[11] Patent Number: 5,875,777
[45] Date of Patent: Mar. 2, 1999

[54] VENTILATOR AND METHOD FOR CONTROLLING SAME TO REPRODUCE A MANUALLY GENERATED BREATHING PATTERN

[75] Inventor: Per-Göran Eriksson, Täby, Sweden

[73] Assignee: Siemens Elema AB, Solna, Sweden

[21] Appl. No.: 842,368

[22] Filed: Apr. 24, 1997

[30] Foreign Application Priority Data

Apr. 26, 1996 [SE] Sweden .................................. 9601611

[51] Int. Cl.[6] .................................................. A61M 16/00
[52] U.S. Cl. .............................. 128/204.21; 128/205.13; 128/204.23
[58] Field of Search .......................... 128/204.21, 204.23, 128/204.28, 205.13, 205.28, 203.12, 203.14

[56] References Cited

U.S. PATENT DOCUMENTS 5,509,406  4/1996  Koek et al. ......................... 128/203.14
5,782,233  7/1998  Nieoe et al. ........................ 128/205.13

FOREIGN PATENT DOCUMENTS 0 570 015  11/1993  European Pat. Off. ........ A62B 27/00

Primary Examiner—John G. Weiss
Assistant Examiner—V. Srivastava
Attorney, Agent, or Firm—Hill & Simpson

[57] ABSTRACT

In a ventilator system and a method for controlling the ventilator system, a hand ventilator is connectable to a patient to impose a manually generated breathing pattern on the patient. A measurement unit is arranged by the hand ventilator to measure at least one of the parameters pressure and flow of the manually generated breathing pattern. The measured parameters are supplied to a memory unit in a regulatory unit, which operates a control unit so as to regulate a valve unit for imposing a mechanically generated breathing pattern, corresponding to the manually generated breathing pattern, on the patient. The measured parameters can be re-scaled in a calculation unit before the control unit controls the valve unit.

10 Claims, 1 Drawing Sheet

VENTILATOR AND METHOD FOR CONTROLLING SAME TO REPRODUCE A MANUALLY GENERATED BREATHING PATTERN

BACKGROUND OF THE INVENTION

1. Field of the Invention

The present invention is directed to a method for controlling a valve unit in a ventilator system and to a ventilator system for implementing the method.

As used herein, "ventilator system" refers to all types of systems capable of delivering a gas to a patient for the purpose of supporting or controlling the patient's breathing.

2. Description of the Prior Art

European Application 570 015 describes a system capable of recording a patient's spontaneous breathing pattern and copying the recorded spontaneous breathing pattern into a ventilator system in order to mechanically reproduce this breathing pattern for ventilating the patient.

Thus, this known system is restricted to spontaneously breathing patients whose pulmonary function is relatively intact. The advantage of recreating the patient's spontaneous breathing pattern is to minimize the patient's discomfort when a breathing gas must be imposed on the patient, e.g, in anesthesia.

In many instances, however, the patient is not breathing spontaneously or the patient's condition is such that the patient requires breathing support to get enough breathing gas. The options usually available are mechanical ventilation (imposed or supportive) by a ventilator system or a breathing pattern manually imposed by a doctor with a hand ventilator. With a hand ventilator, the doctor is able to feel the lung's response and regulate the patient's breathing. Manual ventilation of this kind, however, requires the constant presence of a doctor.

SUMMARY OF THE INVENTION

An object of the present invention is to provide a method for controlling a ventilator unit in a ventilator system in which the aforementioned disadvantages and problems with previous methods are eliminated Another object of the invention is to provide a ventilator system for effective, customized ventilation of a patient with a breathing pattern tailored to the patient's needs to the greatest possible degree.

The above objects are achieved in accordance with the principles of the present invention in a ventilator system and in a method for controlling a valve unit in a ventilator system, wherein a manually generated breathing pattern is measured with respect to at least one of the parameters of pressure, flow and duration, wherein the measured parameters are stored, and wherein the stored parameters are used as reference values for controlling the valve unit in the mechanical generation of a breathing pattern applied to a patient.

When a doctor manually generates a breathing pattern, which the doctor regards, on the basis of the doctor's know-how and experience, as the best breathing pattern for the patient, this breathing pattern can be read and recorded in a memory unit for subsequent use in the generation of a mechanical breathing pattern. The mechanical breathing pattern will then be a copy of the breathing pattern manually generated by the doctor. For example, an anesthetist can in this way determine the breathing pattern the patient is to receive in anesthesia and then have a control system generate it by means of a valve unit. The anesthetist can then devote more attention to the patient's depth of anesthesia, etc.

Pressure, flow and duration in particular are the essential breathing pattern parameters in this context. Here, the method can be performed so the pressure pattern generated by the doctor is mechanically copied by the ventilator unit. Alternatively, the flow pattern or duration can be copied in a like manner. In a more advanced embodiment more than one, or all, of the parameters can be recorded and mechanically reproduced.

The breathing pattern can be recorded over a number of consecutive breathing cycles in order to achieve greater breathing pattern accuracy, and an average value for the included parameters can be calculated and used in controlling the ventilator unit.

In order to achieve optimum ventilation of the patient, re-scaling a parameter, before it is copied for mechanical generation, may be appropriate in certain instances. Examples of re-scaling can be changes in the ratio between inspiratory and expiratory times, tidal volume, respiratory rate, etc.

The doctor can also be given the option of determining whether the pressure pattern or flow pattern is to have priority in mechanical generation.

DESCRIPTION OF THE PREFERRED EMBODIMENTS

Figure 1:
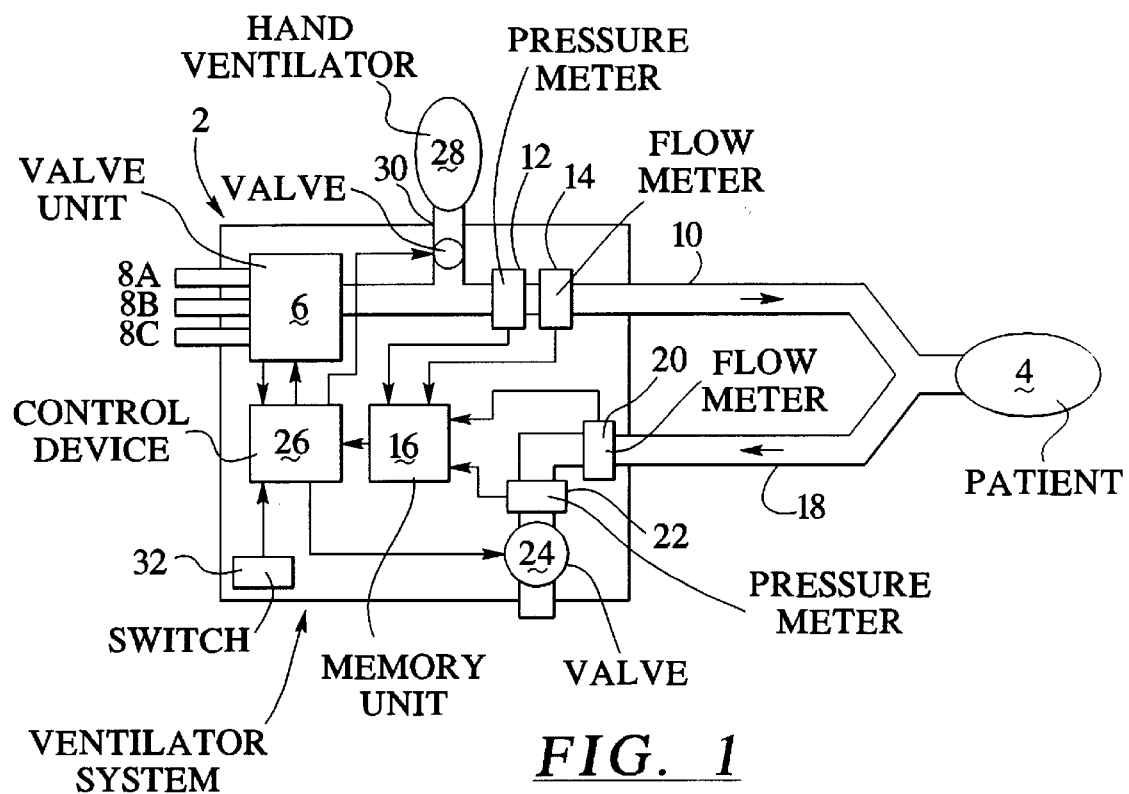
FIG. 1 shows a first embodiment of a ventilator system constructed and operating in accordance with the principles of the present invention.

The ventilator system 2 in FIG. 1 is connected to a patient 4 in order to control or support the patient's breathing. A ventilator unit 6 in the ventilator system 2 regulates and mixes inflowing gases, which are connected via gas connectors 8A, 8B and 8C. The mixed breathing gas is carried in an inspiratory line 10 to the patient 4, then passing a first pressure meter 12 and a first flow meter 14 which send the values measured for pressure and flow to a memory unit 16 in the ventilator system 2. Expired breathing gas is carried away from the patient 4 in an expiratory line 18, then passing a second flow meter 20 and a second pressure meter 22 whose measurement signals are also sent to the memory unit 16. The memory unit 16 contains a timer for determining various intervals and durations for, e.g., the entire breathing cycle, inspiratory time, expiratory time etc. A valve 24 regulates outflow from the expiratory line 18.

A control unit 26 regulates the various functions in the ventilator system 2 and is therefore connected to the valve unit 6, memory unit 16 and the valve 24. Other functions and connections are described below.

A hand ventilator 28 is also arranged in the ventilator system 2 and can be connected to the inspiratory line 10 by a valve 30. In this instance, the valve 30 is controlled by the control device 26 but can also be manually adjusted or actuated in some other way. When the hand ventilator 28 is used, a doctor can impose a breathing pattern, selected by that doctor, on the patient 4 by squeezing the hand ventilator 28. The imposed breathing pattern can be measured with the first flow meter 14 and the first pressure meter 12, and the breathing pattern can be stored in the memory unit 16.

Switching between mechanical ventilation and manual ventilation can be performed with a switch 32.

The switch 32 can be manually actuated by the doctor or can switch automatically between mechanical and manual ventilation according to, e.g., pressure conditions in the hand ventilator 28 and/or time conditions. For example, the switch 32 can be operated so that manual ventilation is always activated when the doctor squeezes the hand ventilator 28, thereby increasing pressure in same, and mechanical ventilation is always activated if no squeezing of the hand ventilator 28 has been registered for a specific period of time. This is especially important to the safety of the patient 4.

Figure 2:
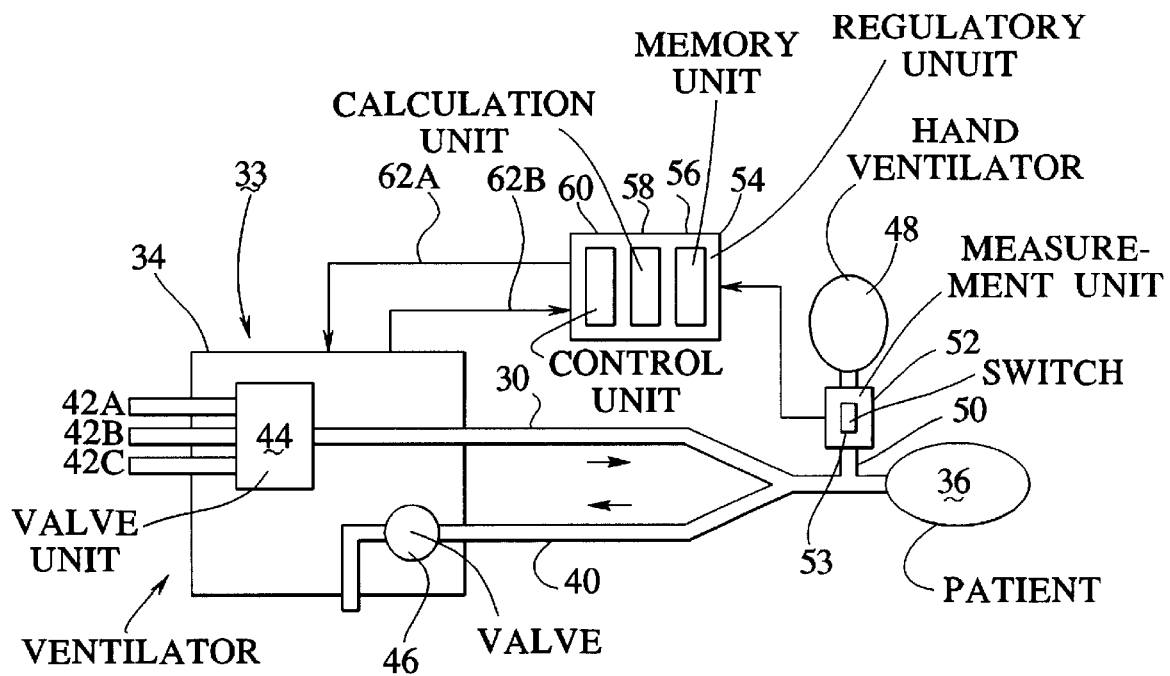
FIG. 2 shows a second embodiment of the ventilator system constructed and operating in accordance with the principles of the present invention.

FIG. 2 shows a second embodiment, designated 33, of the inventive ventilator system. In this embodiment, the system is formed of a number of separate units, wherein a ventilator 34 is connected to a patient 36 in order to supply a breathing gas through an inspiratory line 38 and remove expired breathing gas through an expiratory line 40. The gases to be mixed into breathing gas can be connected to a valve unit 44 in the ventilator 34 by means of three gas connectors 42A, 42B and 42C. As in the above, expired breathing gas is regulated by a valve 46.

In this embodiment, a separate hand ventilator 48 is connected to the patient 36 by a separate gas line 50 in which a measurement unit 52 is arranged. The measurement unit 52 can include both pressure and flow meters. Measurement signals from the measurement unit 52 are sent to a regulatory unit 54 which, with the hand ventilator 48, gas line 50 and measurement unit 52, constitutes an independent apparatus which can be connected to any type of stand-alone breathing assist device, such as all types of ventilators and anesthesia machines.

A memory unit 56, a calculation unit 58 and a control unit 60 are arranged in the regulatory unit 54. The regulatory unit 54 can exchange signals with, in this exemplary embodiment, a ventilator 34 via a first signal line 62A and a second signal line 62B. Measurement values for e.g., flow and pressure determined (by a meter not shown) inside the ventilator 34 are sent from the ventilator unit 34 to the regulatory unit 54, and control signals for the valve unit 44 in the ventilator 34 can be sent from the regulatory unit 54.

In this embodiment, the hand ventilator 48 is connected to the patient 36, and the doctor ventilates the patient 36 with a manual breathing pattern, and the pattern is recorded when the doctor is satisfied with it, and switching can be performed with a switch 53 so the regulatory unit 54 takes over ventilation of the patient 36 by regulating the valve unit 44 in the ventilator 34. A mechanical breathing pattern, which can be identical to the breathing pattern generated manually by the doctor or which can be a breathing pattern which is somewhat revised, e.g. in respect to the relationship between inspiratory and expiratory time, tidal volume or the like, will then be generated One such re-scaling of parameter values can be performed by the doctor, from a control panel (not shown) for the regulatory unit 54.

The measurement unit 52 can also be devised and/or arranged to measure e.g. pressure within the lung or trachea of the patient 36.

Combinations of the two embodiments can be made where appropriate.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for controlling a valve unit in a ventilator system comprising the steps of:

manually generating a breathing pattern, said breathing pattern including pressure, flow and duration parameters;

measuring at least one of said parameters of said breathing pattern to obtain a measured parameter;

storing said measured parameter as a stored parameter; and operating a valve unit in a ventilator system using said stored parameter as a reference value for reproducing said manually generated breathing pattern as a mechanically generated breathing pattern.

2. A method as claimed in claim 1 wherein the step of measuring said at least one parameter comprises measuring said at least one parameter over a plurality of consecutive breathing cycles of said manually generated breathing pattern, generating an average value of said at least one parameter over said plurality of consecutive breathing cycles, and storing said average value as said stored parameter and using said average value as said reference value.

3. A method as claimed in claim 1 comprising the additional step of re-scaling said stored parameter to produce said reference value.

4. A ventilator system comprising:

a source of breathing gas;

means adapted for delivering said breathing gas to a patient in a breathing gas flow;

valve means for imposing a breathing pattern on said breathing gas flow, said breathing gas flow with said breathing pattern imposed thereon having parameters of gas pressure, gas flow and duration;

measurement means for measuring at least one of said parameters for producing at least one measured parameter;

memory means for storing said at least one measured parameter as at least one stored parameter;

control means for controlling said valve means according to said at least one stored parameter;

switch means, connected to said memory means and to said control means for, in a first switching state, causing said memory means to store said at least one measured parameter as said at least one stored parameter and for, in a second switching state, causing said control means to control said valve means according to said at least one stored parameter; and manually-operated ventilator means for generating a manual breathing pattern as said selected breathing pattern, with said switching means in said first switching state for storing a parameter of said manually generated breathing pattern as said stored parameter.

5. A ventilator system as claimed in claim 4 wherein said memory means comprises means for storing said at least one parameter over a plurality of consecutive breathing cycles of said breathing pattern, and further comprising calculating means for calculating an average value of said at least one parameter over said plurality of consecutive breathing cycles, said control means comprising means for using said average value for controlling said valve means.

6. A ventilator system as claimed in claim 4 wherein said control means comprises means for re-scaling said at least one stored value for use in controlling said valve means.

7. A ventilator system as claimed in claim 4 comprising a stand-alone breathing assist device containing said valve means, and a separate regulatory unit, connectable to said stand-alone breathing assist unit, containing said manually-operable ventilator means, said measurement means, said memory means and said control means.

8. A ventilator system comprising:
   means for manually generating a breathing pattern, said breathing pattern including pressure, flow and duration parameters;
   measurement means for measuring at least one of said parameters of said breathing pattern to obtain a measured parameter;
   memory means for storing said measured parameter as a stored parameter;
   a valve unit; and
   means for operating said valve unit using said stored parameter as a reference value for reproducing said manually generated breathing pattern as a mechanically generated breathing pattern.

9. A ventilator system as claimed in claim 8 wherein said measurement means comprises means for measuring said at least one parameter comprises measuring said at least one parameter over a plurality of consecutive breathing cycles of said manually generated breathing pattern, means for generating an average value of said at least one parameter over said plurality of consecutive breathing cycles, wherein said memory means comprises means for storing said average value as said stored parameter and wherein said means for operating said valve unit uses said average value as said reference value.

10. A ventilator system as claimed in claim 8 further comprising means for re-scaling said stored parameter to produce said reference value.

* * * * *